(12) United States Patent
Kinlen et al.

(10) Patent No.: US 11,796,451 B2
(45) Date of Patent: Oct. 24, 2023

(54) SYSTEMS AND METHODS FOR MEASURING GALVANIC CORROSION POTENTIAL

(71) Applicant: The Boeing Company, Chicago, IL (US)

(72) Inventors: Patrick J. Kinlen, Fenton, MO (US); Waynie M. Schuette, Troy, IL (US)

(73) Assignee: THE BOEING COMPANY, Arlington, VA (US)

( * ) Notice: Subject to any disclaimer, the term of this patent is extended or adjusted under 35 U.S.C. 154(b) by 375 days.

(21) Appl. No.: 17/281,164

(22) PCT Filed: Jan. 18, 2019

(86) PCT No.: PCT/US2019/014376
§ 371 (c)(1),
(2) Date: Mar. 29, 2021

(87) PCT Pub. No.: WO2020/149862
PCT Pub. Date: Jul. 23, 2020

(65) Prior Publication Data
US 2021/0349008 A1 Nov. 11, 2021

(51) Int. Cl.
*G01N 17/02* (2006.01)
*G01N 27/403* (2006.01)
*G01N 33/44* (2006.01)

(52) U.S. Cl.
CPC ........... *G01N 17/02* (2013.01); *G01N 27/403* (2013.01); *G01N 33/442* (2013.01)

(58) Field of Classification Search
CPC ............................................. G01N 17/02–046
See application file for complete search history.

(56) References Cited

U.S. PATENT DOCUMENTS

2013/0280416 A1  10/2013  Hack et al.

FOREIGN PATENT DOCUMENTS

| CN | 106940277 A | 7/2017 |
| CN | 107576709 A | 1/2018 |

(Continued)

OTHER PUBLICATIONS

Google patent translation of Chen et al. CN 106940277 A, downloaded Jun. 1, 2023, patetn date Nov. 7, 2017 (Year: 2017).*

(Continued)

*Primary Examiner* — Alexander S Noguerola
(74) *Attorney, Agent, or Firm* — MH2 Technology Law Group LLP

(57) ABSTRACT

A system for measuring corrosion includes a first electrode configured to be connected to a first structure and a second electrode configured to be connected to a second structure. The first and second structures are galvanically-coupled together, and the first and second structures are made of different materials. A chamber is configured to run through one or more cycles while the first electrode, the first structure, the second electrode, and the second structure are positioned inside the chamber. A measurement device is configured to receive data from the first and second electrodes and to measure one or more parameters based at least partially upon the data. A level of corrosion on the first structure, the second structure, or both is configured to be determined based at least partially upon the one or more parameters.

19 Claims, 6 Drawing Sheets

(56) References Cited

FOREIGN PATENT DOCUMENTS

| KR | 2011-010880 A | 10/2011 | |
|---|---|---|---|
| WO | WO 2016053743 A1 * | 4/2016 | ............... G01B 7/34 |
| WO | WO 2018042404 A1 * | 3/2018 | ............. G01N 19/04 |

OTHER PUBLICATIONS

Online article on Machinery Lubrication website entitled "Fretting Wear in Lubricated Systems" by E.C. Fitch (Jan. 2005) https://www.machinerylubrication.com/Read/693/fretting-wear (Year: 2005).*

Dila Ram Banjade Master of Science thesis entitled "Galvanic Corrosion of Magnesium Coupled to Steel at High Cathode-to-Anode Area Ratios," Brigham Young University, 2015 (Year: 2015).*

Thesis of Aarti Shenoy entitled, "The Effect of Surface Roughness on the Fretting Corrosion of 316L Stainless Steel Biomaterial Surfaces," Syracuse University, Dec. 2014 (Year: 2014).*

Nickitas-Etienne, Athina (PCT Authorized Officer), Notification Concerning Transmittal of International Preliminary Report on Patentability dated Jul. 29, 2021 in corresponding International Application No. PCT/US2019/014376, 9 pages.

International Search Report and Written Opinion of the International Searching Authority dated Nov. 6, 2019, 17 pages.

Hakansson, "Galvanic Corrosion of Aluminum Carbon Composite Systems," Electronic Theses and Dissertations, Jan. 2016, pp. 1-334.

* cited by examiner

SYSTEMS AND METHODS FOR MEASURING GALVANIC CORROSION POTENTIAL

CROSS REFERENCE TO RELATED APPLICATIONS

The present application is the national stage entry of International Patent Application No. PCT/US2019/014376, filed on Jan. 18, 2019, the disclosure which is hereby incorporated by reference in its entirety.

FIELD OF THE DISCLOSURE

The present disclosure is directed to systems and methods for measuring corrosion. More particularly, the present disclosure is directed to systems and methods for measuring galvanic corrosion potential on a component.

BACKGROUND

Corrosion may be understood as the chemical and/or electrochemical degradation of materials due to reaction with their environment. General corrosion, as the name implies, tends to proceed more or less uniformly over an exposed surface of a material without appreciable localization of the attack. General corrosion typically proceeds at a relatively slow, predictable rate. In contrast, galvanic corrosion tends to be a more localized effect at and/or near electrical and/or physical contact points between dissimilar materials in the presence of a conductive medium, such as an electrolyte. Galvanic corrosion can proceed at relatively high and/or unpredictable rates, potentially causing a component not to perform as intended.

In one particular example, localized galvanic corrosion may form on an aluminum alloy honeycomb core structure. More particularly, the localized galvanic corrosion may form on the edges and surfaces near the bond edges between the aluminum alloy honeycomb core structure and a carbon-fiber reinforced plastic (CFRP) structure. Bond primers and chromate primers are oftentimes used; however, they may not be sufficient to prevent corrosion in these areas due to galvanic processes driven by the CFRP structure.

Therefore, it would be desirable to have improved systems and methods for measuring and preventing galvanic corrosion.

SUMMARY

A system for measuring corrosion is disclosed. The system includes a first electrode configured to be connected to a first structure and a second electrode configured to be connected to a second structure. The first and second structures are galvanically-coupled together, and the first and second structures are made of different materials. A chamber is configured to run through one or more cycles while the first electrode, the first structure, the second electrode, and the second structure are positioned inside the chamber. A measurement device is configured to receive data from the first and second electrodes and to measure one or more parameters based at least partially upon the data. A level of corrosion on the first structure, the second structure, or both is configured to be determined based at least partially upon the one or more parameters.

In at least one implementation, the measurement device is positioned outside of the chamber.

In at least one implementation, the first structure includes a honeycomb structure made of metal.

In at least one implementation, the second structure includes a plate made of plastic. In at least one implementation, the first structure includes a honeycomb structure made of aluminum, and the second structure includes a plate made of carbon-fiber reinforced plastic.

In at least one implementation, the second structure has a plurality of perforations formed therethrough.

In at least one implementation, the measurement device is or includes a potentiostat, the first electrode is or includes a working electrode, the second electrode is or includes a reference electrode, and the one or more parameters include a voltage difference between the first and second structures.

In at least one implementation, the one or more cycles include a wet cycle, a dry cycle, a humid cycle, or a combination thereof.

In at least one implementation, the first and second structures are part of a component in a vehicle.

In at least one implementation, the first and second structures are part of a component in an aircraft.

In another example, the system includes a first electrode configured to be connected to a first structure. The first structure is a honeycomb structure made of aluminum. The system also includes a second electrode configured to be connected to a second structure. The second structure is a plate made of carbon-fiber reinforced plastic, and the first and second structures are galvanically-coupled together. The system also includes a chamber configured to run through a wet cycle and a dry cycle while the first electrode, the first structure, the second electrode, and the second structure are positioned inside the chamber. The system also includes a potentiostat configured to receive data from the first and second electrodes and to measure a voltage difference between the first and second structures based at least partially upon the data. A level of corrosion on the first structure, the second structure, or both is configured to be determined based at least partially upon the voltage difference.

In at least one implementation, the first and second structures are configured to be sprayed with a liquid salt solution having a temperature from about 30° C. to about 40° C. during the wet cycle, and the first and second structures are configured to be blown with air having a temperature from about 20° C. to about 50° C. during the dry cycle.

In at least one implementation, the liquid salt solution includes 5% NaCl pH 3 HAc.

In at least one implementation, the chamber is also configured to run through a humid cycle while the first electrode, the first structure, the second electrode, and the second structure are positioned inside the chamber, the first and second structures are configured to be blown with air having a temperature from about 20° C. to about 50° C. during the dry cycle, and the air blown during the humid cycle has a greater humidity than the air blown during the dry cycle.

In at least one implementation, the first structure is a first portion of the honeycomb structure after the honeycomb structure has been cut into two portions.

A method for measuring corrosion is also disclosed. The method includes connecting a first electrode to a first structure and connecting a second electrode to a second structure. The first and second structures are galvanically-coupled together, and the first and second structures are made of different materials. The first electrode, the first structure, the second electrode, and the second structure are positioned in a chamber. One or more cycles are run in the chamber. One or more parameters related to the first and second structures are measured based on data received from the first and second electrodes. A level of corrosion on the first structure, the second structure, or both is configured to be determined based at least partially upon the one or more parameters.

In at least one implementation, the first structure and the second structure are part of a component that also includes a third structure, and the first structure is coupled to and positioned between the second and third structures. The method may also include cutting through the first structure to create first and second portions of the component, the first portion of the component including a first portion of the first structure coupled to the second structure, and the second portion of the component including a second portion of the first structure coupled to the third structure.

In at least one implementation, positioning the first and second structures in the chamber includes positioning the first portion of the component in the chamber.

In at least one implementation, the method also includes applying a sealant to a connection between the first electrode and the first structure before the first portion of the component is positioned in the chamber.

In at least one implementation, the level of corrosion is configured to be measured in real-time when the first structure and the second structure are in service.

It is to be understood that both the foregoing general description and the following detailed description are exemplary and explanatory only and are not restrictive of the present teachings, as claimed.

BRIEF DESCRIPTION OF THE DRAWINGS

The accompanying drawings, which are incorporated in and constitute a part of this specification, illustrate aspects of the present teachings and together with the description, serve to explain the principles of the present teachings.

Figure 1:
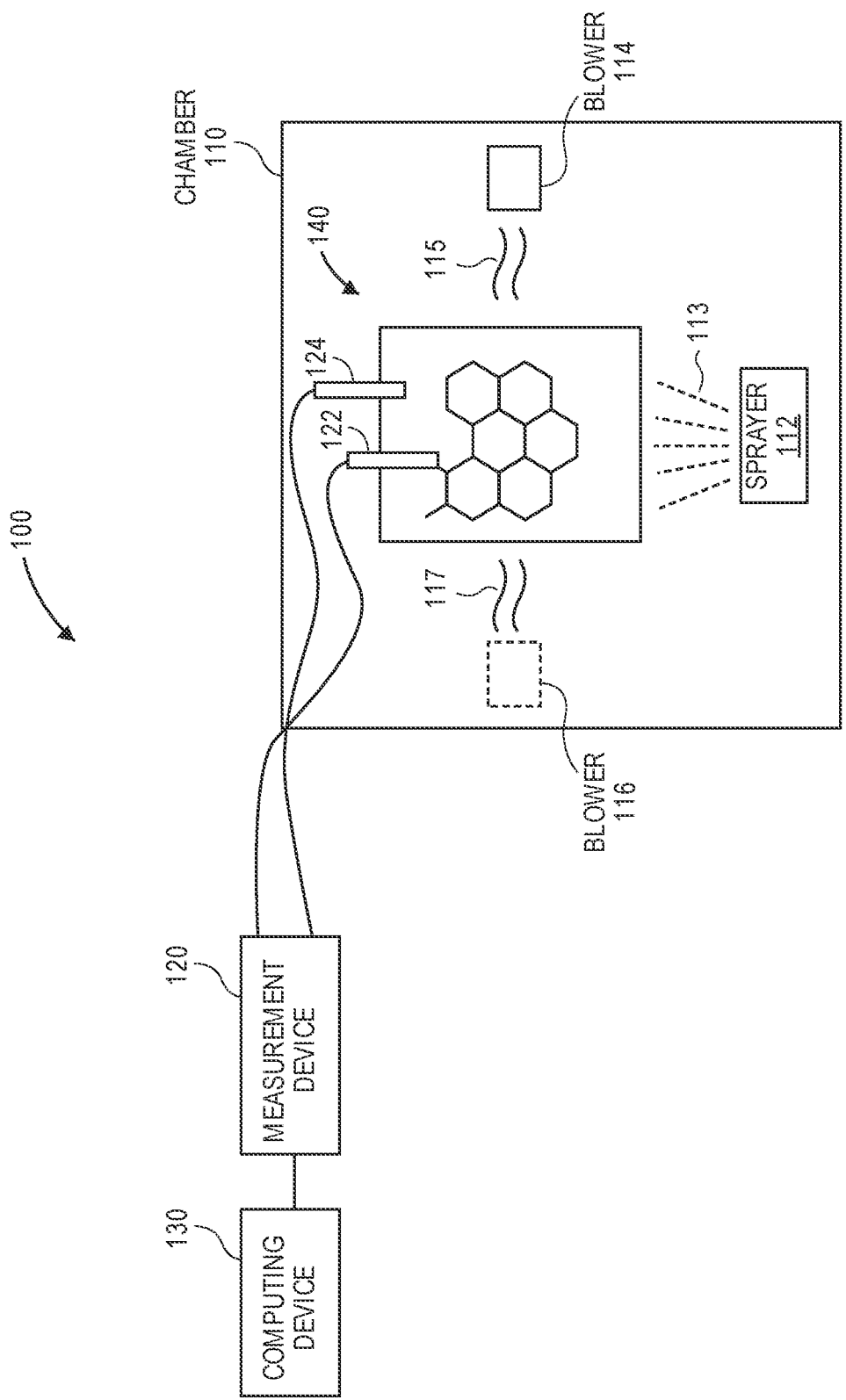
FIG. 1 illustrates a system for measuring corrosion on a component.

It should be noted that some details of the figures have been simplified and are drawn to facilitate understanding rather than to maintain strict structural accuracy, detail, and scale.

DESCRIPTION

Reference will now be made in detail to the present teachings, examples of which are illustrated in the accompanying drawings. In the drawings, like reference numerals have been used throughout to designate identical elements. In the following description, reference is made to the accompanying drawings that form a part thereof, and in which is shown by way of illustration specific examples of practicing the present teachings. The following description is, therefore, merely exemplary.

Known galvanic corrosion resistance testing generally cannot be used for parts because the part configuration is fixed, and the position of the connection between the carbon-fiber reinforced plastic (CFRP) and the metal may not be known and/or cannot be controlled. Current systems connect a wire between two electrodes to separately test the materials. Further, current systems cannot provide simulation of cyclic corrosion testing. In known testing systems, the connections are on top of the testing apparatus. Current flow between two parts goes through a zero resistance ammeter. This causes leakage current inside the part, so a user cannot measure a pre-connected part. The following system addresses these issues.

FIG. 1 illustrates a system 100 for measuring corrosion on a component 140. The system 100 includes a chamber 110 in which the component 140 can be positioned. The chamber 110 can be or include a cyclic corrosion chamber. Thus, the chamber 110 can be configured to expose the component 140 to one or more cycles. The cycles can be or include a wet cycle, a dry cycle, a humid cycle, or a combination thereof. Other cycles can include a prohesion cycle, a corrosion/weathering cycle, an automotive CCT exposure cycle, or a Japanese automotive cyclic corrosion test cycle. The prohesion cycle is defined by the ASTM G85 Annex 5 standard, and the corrosion/weathering cycle is defined by the ASTM D5894-16 standard.

The wet cycle may include spraying the component 140 with a liquid using a sprayer 112 inside the chamber 110. The liquid can be a liquid salt solution (e.g., 5% NaCl pH 3 HAc). The liquid can have a temperature from about 25° C. to about 45° C., about 30° C. to about 40° C., or about 35° C. The chemical composition and/or the temperature of the liquid salt solution can simulate an environment to which the component 140 may be exposed when in use.

The dry cycle can include blowing the component 140 with a gas 115 using a first blower 114 inside the chamber 110. The gas 115 can be air. The gas 115 can have a temperature from about 20° C. to about 50° C. The gas 115 can have a humidity from about 20% to about 90% RH or about 30% to about 80% RH. The temperature and humidity can simulate an environment to which the component 140 may be exposed when in use.

The humid cycle can include blowing the component 140 with a gas 117 using a second blower 116 inside the chamber 110. In an alternative implementation, a single blower can be used for the dry cycle and the humid cycle. The gas 117 may be air. The gas can have a temperature from about 20° C. to about 50° C. The gas used during the humid cycle has a humidity that is greater than the humidity of the gas blown in the dry cycle. For example, the humidity of the gas can be from about 30% to about 95% RH or about 40% to about 100% RH during a particular humid cycle. The temperature and humidity simulates an environment to which the component 140 may be exposed when in use.

The system 100 also includes a measurement device 120. The measurement device 120 can be or include a potentiostat, an ammeter, an ohmmeter, voltmeter, or a combination thereof. The measurement device 120 can include a first (e.g., working) electrode 122 and a second (e.g., reference) electrode 124. As shown, the first electrode 122 and the second electrode 124 can each be positioned within the chamber 110 and coupled to the component 140, as described in greater detail below. The first electrode 122 can be the electrode where the potential is controlled and where the current is measured. The first electrode 122 can be made of an inert material (e.g., gold, platinum, or glassy carbon). The first electrode 122 can serve as a surface on which the electrochemical reaction takes place. During corrosion testing, the first electrode 122 can be a sample of the corroding metal. However, the first electrode 122 may not be the actual metal structure being tested. Instead, a small sample can be used to represent the structure. The first electrode 122 can be bare metal or coated. The second electrode 124 can be used to measure the potential of the first electrode 122. The second electrode 124 can have a constant electrochemical potential as long as no current flows through it. The second electrode 124 can be or include a saturated calomel electrode (SCE), a silver/silver chloride (Ag/AgCl) electrodes, or the like, which may facilitate measuring the potential of the first electrode 122.

The ammeter can be configured to measure the current flowing between two or more portions of the component 140. The ohmmeter can be configured to measure the resistance between two or more portions of the component 140. The effects of measuring the current and/or resistance are discussed in greater detail below.

The system 100 can also include a computing device 130 that is coupled to and/or in communication with the measurement device 120. The computing device 130 can be configured to receive and process the data measured by the measurement device 120 over one or more of the cycles. The computing device 130 can be able to generate results (e.g., see the graphs in FIGS. 5 and 6) based at least partially upon the data measured by the measurement device 120. This is discussed in greater detail below.

Figure 2:
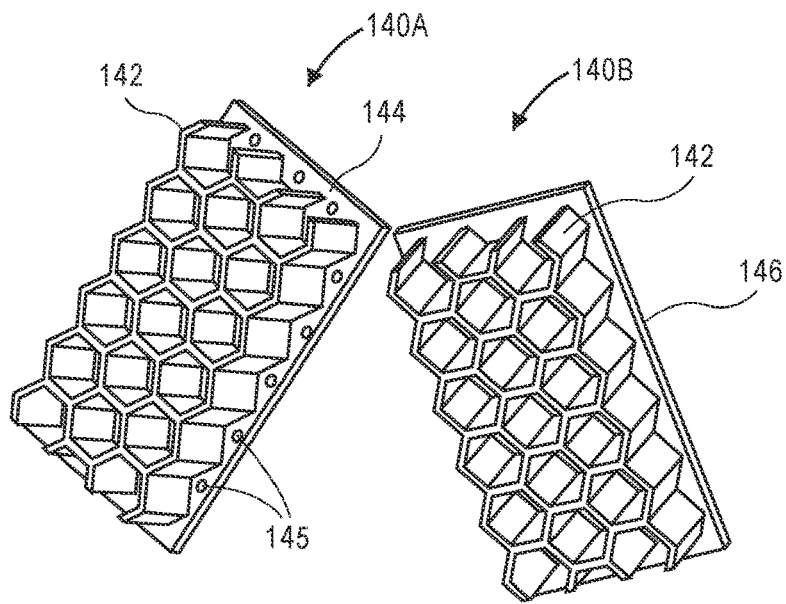
FIG. 2 illustrates a top view of a portion of the component after a first structure of the component is cut into two parts.

FIG. 2 illustrates a top view of the component 140 after the component 140 is cut into first and second portions 140A, 140B. In another example, the component 140 may be or include metal containing composite structures, metal fasteners in contact with composites, materials that have dissimilar potentials, or the like. Thus, the component 140 can be or include any two or more structures that are galvanically-coupled together. As used herein, two components are galvanically-coupled together when the components have dissimilar potentials and are coupled/connected by a conductive pathway.

The component 140 includes a first structure 142. As shown, the first structure 142 can be or include a honeycomb structure that is made of a first material. The first material may be or include a metal such as aluminum, titanium steel, copper, cadmium, nickel, silver, zinc, magnesium, or the like, which can contribute to galvanic corrosion when coupled to the second structure 144 in the presence of one or more of the cycles described above. As shown, the first structure 142 can be cut (e.g., in half) to separate the component 140 into two portions 140A, 140B. Cutting the first structure 142 can make it easier to connect one of the electrodes 122, 124 to the first structure 142, as shown in FIG. 3 and described in greater detail below.

The component 140 also includes a second structure 144 and a third structure 146. The second and third structures 144, 146 can be or include plates made of a second material. The second material can be or include a carbon-fiber reinforced plastic (CFRP), metal containing composite materials (e.g., nickel and steel), or the like. The second structure 144 can have a plurality of perforations 145 formed therethrough and may be referred to as the "tool side" or "perforated side" of the component 140. The third structure 146 can or may not have perforations formed therethrough and may be referred to as the "bag side" of the component 140. The perforations can expose the carbon fibers in the CFRP material, and an oxygen reduction reaction can occur on the exposed carbon fibers, accelerating galvanic corrosion on the honeycomb core. This effect can be prevented on the bag side where there is no exposed carbon fiber.

The first structure 142 can be coupled to and/or positioned between the second and third structures 144, 146. The first structure 142 can be (e.g., galvanically) coupled to the second and third structures 144, 146 using aluminum containing adhesives or mechanical contact using a non-conductive adhesive. The first portion 140A of the component 140 can include part of the first structure 142 coupled to the second structure 144, and the second portion 140B can include the other part of the first structure 142 coupled to the third structure 146. The component 140, including the first structure 142, the second structure 144, and/or the third structure 146 can be part of a vehicle (e.g., an aircraft).

Figure 3:
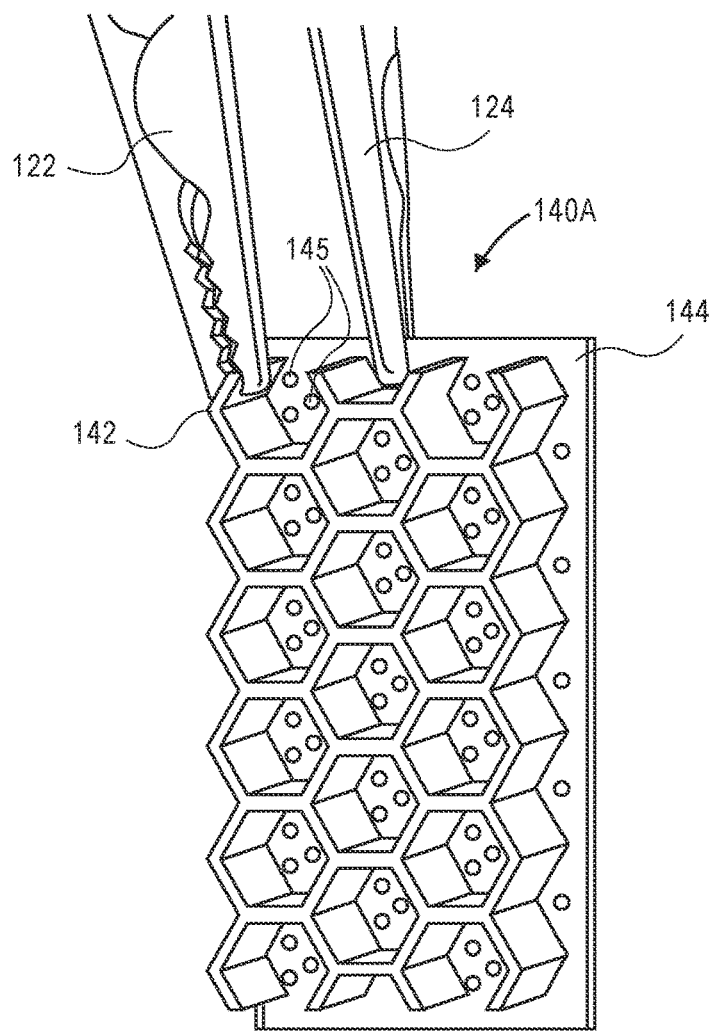
FIG. 3 illustrates a top view of the first structure and a second structure of the component, after the first structure is cut, with a first electrode coupled to the first structure and a second electrode coupled to the second structure.

FIG. 3 illustrates a top view of the first portion 140A of the component 140 (from FIG. 2) with the first (e.g., working) electrode 122 coupled to the first structure 142 and the second (e.g., reference) electrode 124 coupled to the second structure 144. Although not shown, it will be appreciated that the first electrode 122 and the second electrode 124 can be coupled to the second portion 140B of the component 140 in a similar manner. For example, the first electrode 122 can be coupled to the first structure 142, and the second electrode 124 can be coupled to the third structure 146.

Figure 4:
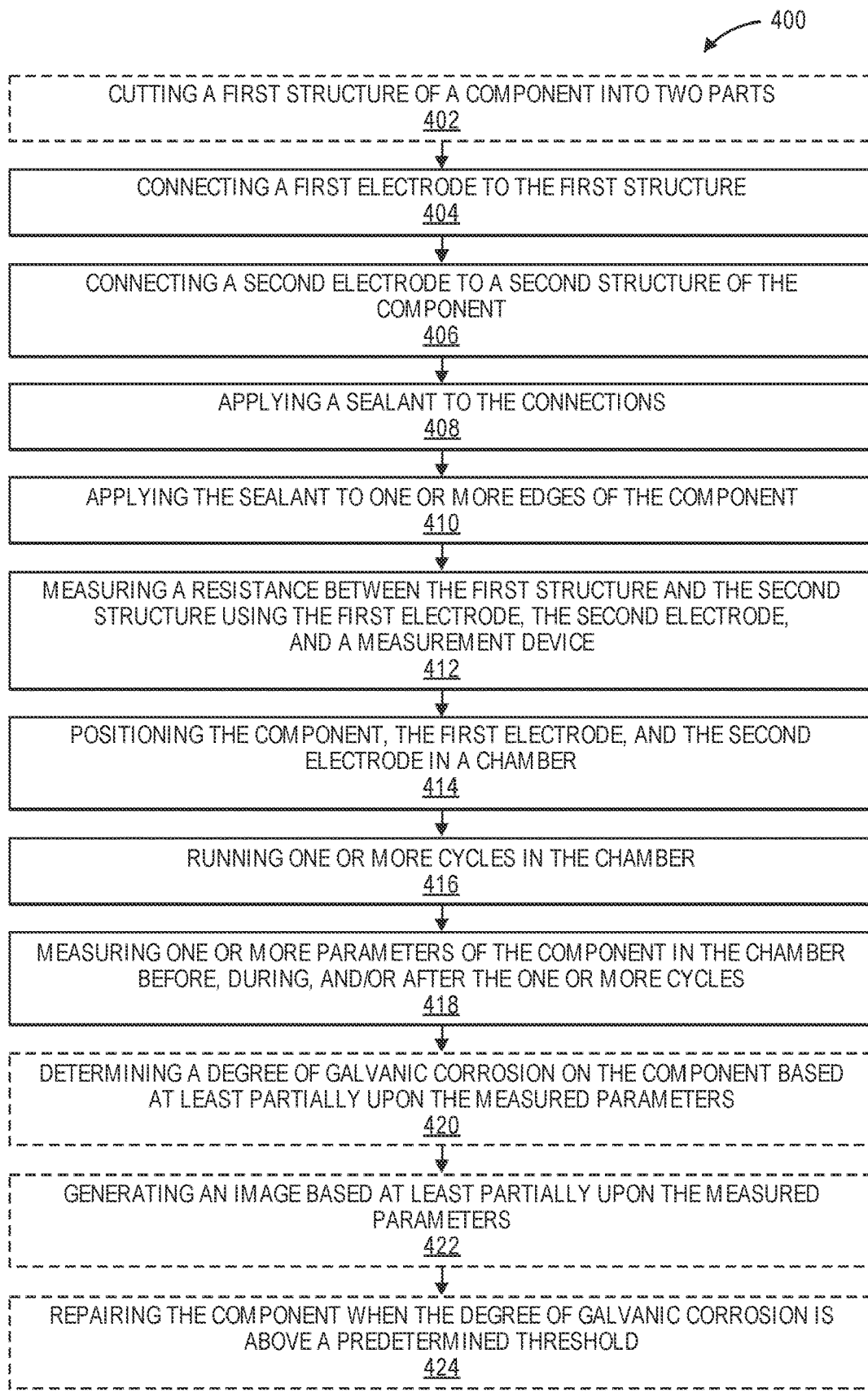
FIG. 4 illustrates a flowchart of a method for measuring corrosion on the component.

FIG. 4 illustrates a flowchart of a method 400 for measuring corrosion on the component 140. More particularly, the method 400 described is for measuring corrosion on the first portion 140A of the component 140; however, as will be appreciated, the method 400 can also be used in a similar manner to measure the corrosion on the second portion 140B of the component 140. In at least one example, the method 400 can be used to measure/determine the corrosion on the component 140 in real-time (e.g., when the component 140 is in service, such as when the component 140 is part of an aircraft that is in flight).

The method 400 can include cutting the first structure 142 of the component 140 into the two separate parts, as at 402. In an alternative implementation, the cutting may be omitted, and the component 140 can remain in one piece for the remainder of the method 400.

The method 400 also includes connecting the first electrode 122 to the first structure (e.g., the aluminum honeycomb) 142, as at 404. The method 400 can also include connecting the second electrode 124 to the second structure (e.g., the CFRP plate) 144, as at 406.

The method 400 also includes applying a sealant to the connection between the first electrode 122 and the first structure (e.g., the aluminum honeycomb) 142 and/or to the connection between the second electrode 124 and the second structure (e.g., the CFRP plate) 144, as at 408. The sealant can be or include an adhesive polyurethane. The sealant serves to isolate the electrical connections from the corroding environment.

The method 400 also includes applying the sealant to one or more edges of the first structure 142 and/or the second structure 144, as at 410. The sealant can be the same type of sealant used to seal the connections or a different type of sealant. The sealant serves to prevent the edges of the first structure 142 and/or the second structure 144 from contributing to the galvanic effect. The sealant can be applied to the edges before or after the sealant is applied to the connections.

The method 400 also includes measuring a resistance between the first structure 142 and the second structure 144 using the measurement device 120 (e.g., when the measurement device 120 functions as an ohmmeter), as at 412. The resistance can be measured after the connections are made and before the sealant is applied or after the connections are made and after the sealant is applied. The resistance can be measured before the cycles begin in the chamber 110. Measuring the electrical resistance at this point can allow the user to determine if there is an electrical connection between the first and second structures 142, 144. The electrical resistance can be measured later in the method 400 to determine if the electrical connection changes.

The method 400 also includes positioning (e.g., the first portion 140A of) the component 140, the first electrode 122, and the second electrode 124 into the chamber 110, as at 414. The method 400 can also include running one or more cycles in the chamber 110 while the (e.g., first portion 140A of) the component 140, the first electrode 122, and the second electrode 124 are in the chamber 110, as at 416. As described above, the cycles can be or include a wet cycle, a dry cycle, a humid cycle, or a combination thereof. For example, the process can alternate between wet and dry cycles. The wet cycle can last from about 15 minutes to about 2 hours or about 30 minutes to about 1 hour (e.g., about 45 minutes). The dry cycle can last from about 30 minutes to about 4 hours or about 1 hour to about 3 hours (e.g., about 2 hours). The humid cycle can last from about 1 hour to about 5 hours or about 2 hours to about 4 hours (e.g., about 3 hours and 15 minutes).

The method 400 also includes measuring one or more parameters of (e.g., the first portion 140A of) the component 140 in the chamber 110 before, during, and/or after the one or more cycles, as at 418. The parameters can be measured in real-time. In at least one implementation, the parameters may be sensed/measured by the two electrodes 122, 124 in the chamber 110 and transmitted (e.g., through wires) to the measurement device 120, which can be outside the chamber 110. As described above, the parameter(s) may be or can include a voltage/potential difference between the first and second structures 142, 144, a resistance between the first and second structures 142, 144, a current flowing between the first and second structures 142, 144, or a combination thereof. The current and/or resistance can be used to estimate the extent of the galvanic corrosion on the structures 142, 144. Measuring galvanic current in site can allow the user to determine how galvanic corrosion worsens with environmental exposure.

The method 400 also includes determining a degree/level of (e.g., galvanic) corrosion on the (e.g., first portion 140A of) the component 140 based at least partially upon the measured parameters, as at 420. This can include determining the degree/level of (e.g., galvanic) corrosion on the first structure 142 and/or the second structure 144. More particularly, the galvanic current can be estimated and integrated over time to estimate the coulombs of charge passed and the amount of metal corroded.

The method 400 can also include generating an image or video (e.g., a graph—see FIGS. 5 and 6) based at least partially upon the measured parameters, as at 422. The image or video may be generated by the measurement device 120 or the computing device 130.

The method 400 can also include repairing the component 140 if the degree/level of (e.g., galvanic) corrosion is above a predetermined threshold, as at 424. In addition, the design of future components may be modified, in response to the degree/level of (e.g., galvanic) corrosion, to reduce the degree/level of corrosion in the future components.

Figure 5:
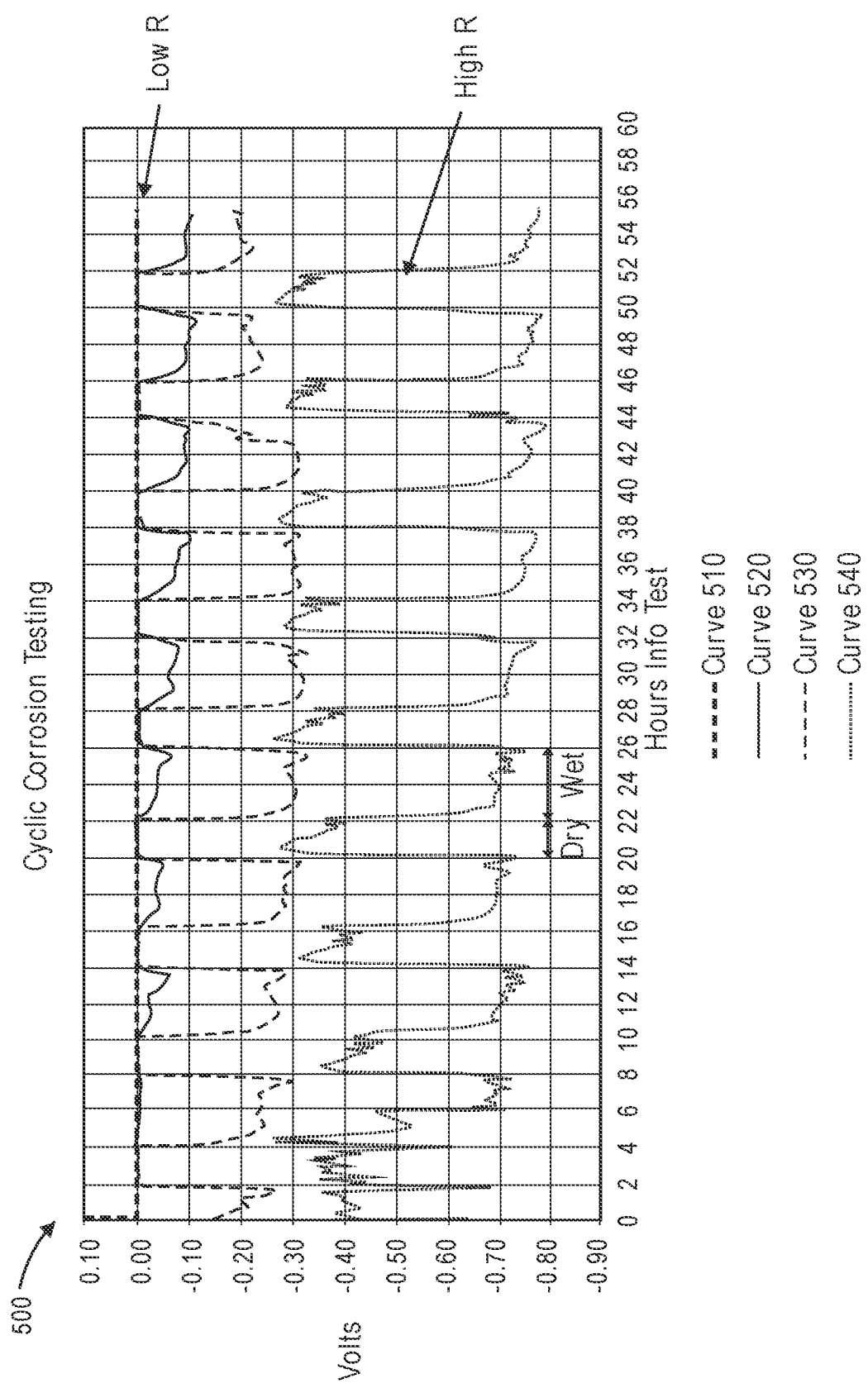
FIG. 5 illustrates a graph showing voltage/potential vs. time during cyclic corrosion testing.

FIG. 5 illustrates a graph 500 showing voltage/potential vs. time during cyclic corrosion testing. The graph 500 shows data for four different components that were tested. The curve 510 is for a first portion of a component (e.g., including the first structure 142 and the second structure 144). Thus, the first portion of the component in curve 510 is the perforated/tool side. The first portion of the component in curve 510 has a resistance of 6.7Ω. The curve 520 is for a second portion of a component (e.g., including the first structure 142 and the third structure 146). Thus, the second portion of the component in curve 520 is the bag side. The second portion of the component in curve 520 has a resistance of 17 kΩ. The curve 530 is for a first portion of a component (e.g., including the first structure 142 and the second structure 144). Thus, the first portion of the component in curve 530 is the perforated/tool side. The first portion of the component in curve 530 has a resistance of 2.9 kΩ. The curve 540 is for a second portion of a component (e.g., including the first structure 142 and the third structure 146). Thus, the second portion of the component in curve 540 is the bag side. The second portion of the component in curve 540 has a resistance of 2.3 MΩ.

As shown, the measured voltage/potential (e.g., from step 418 above) is closer to 0V during the dry cycles and farther from 0V (i.e., higher voltage) during the wet cycles. The measured voltage/potential correlates directly with the resistance of the component. Higher voltage/potential can indicate higher resistance, and higher resistance can indicate lower galvanic current. Conversely, lower voltage/potential can indicate lower resistance, and lower resistance can indicate higher galvanic current. The first portion of the component in the first curve 510 has the lowest resistance. This is undesirable because it indicates higher galvanic current, which can be due to or lead to higher levels of corrosion. The second portion of the component in the curve 540 has the highest resistance. This is more desirable because it indicates lower galvanic current, which can be due or lead to lower levels of corrosion.

Figure 6:
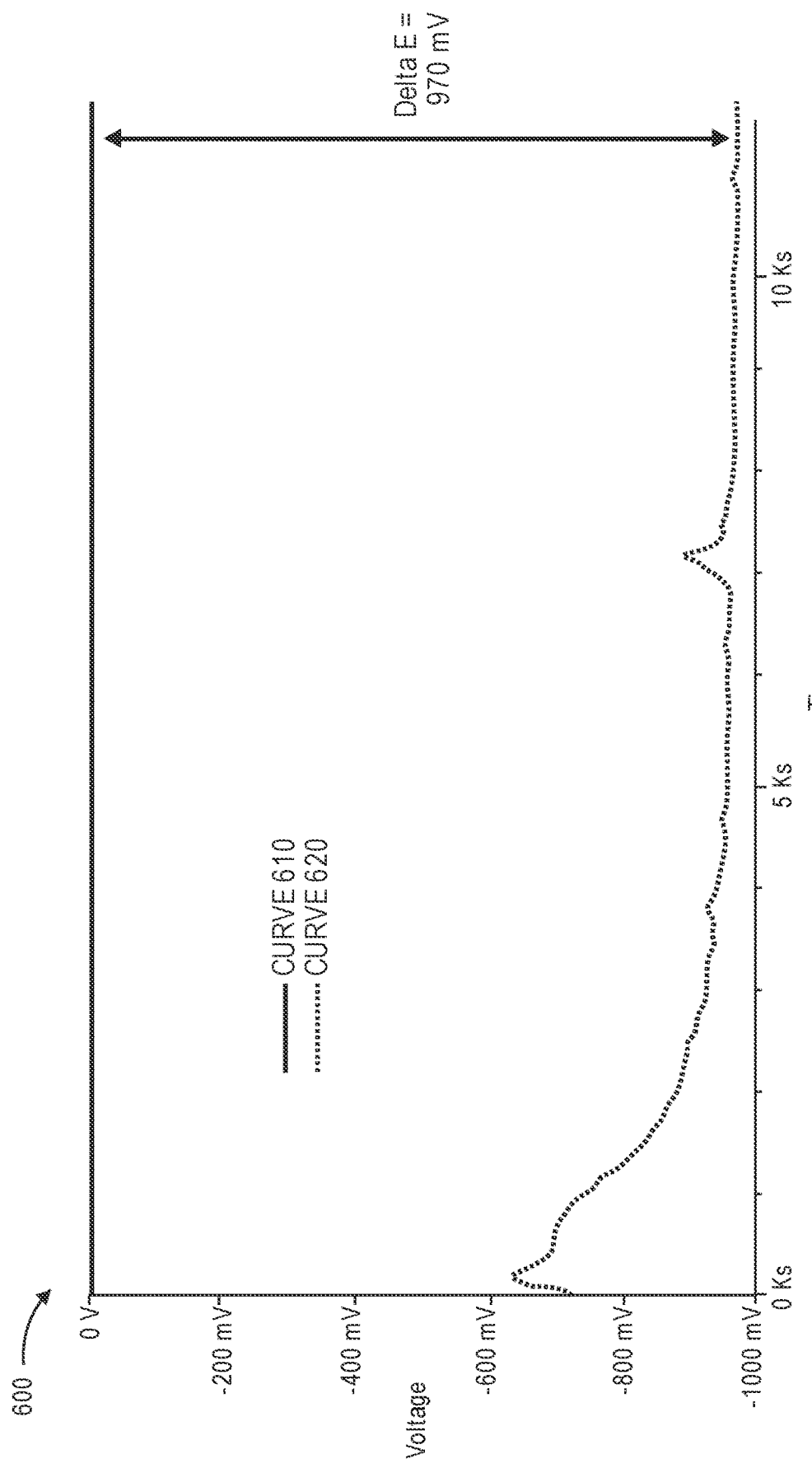
FIG. 6 illustrates another graph showing voltage/potential vs. time during an immersion test.

FIG. 6 illustrates another graph 600 showing voltage/potential vs. time during cyclic corrosion testing. FIG. 6 differs from FIG. 5 in that FIG. 6 represents an immersion experiment, whereas FIG. 5 represents a cyclic experiment. The graph 600 shows data for two different components that were tested. The curve 610 is for a first portion of a component (e.g., including the first structure 142 and the second structure 144). Thus, the first portion of the component in curve 610 is the perforated/tool side. As shown, on the perforated/tool side, the first structure (e.g., aluminum) and the second structure (e.g., CFRP material) are at substantially the same voltage/potential. This may represent a high galvanic corrosion rate.

The curve 620 is for a second portion of a component (e.g., including the first structure 142 and the third structure 146). Thus, the second portion of the component in curve 620 is the bag side. As shown, on the bag side, the first structure (e.g., aluminum) and the third structure (e.g., CFRP material) are at different voltages/potentials. This may represent a low galvanic corrosion rate. The absolute electrical potential of the curve 620 can be a function of the alloy, sensitization, electrolyte, corrosivity of the electrolyte, or a combination thereof.

Figure 7:
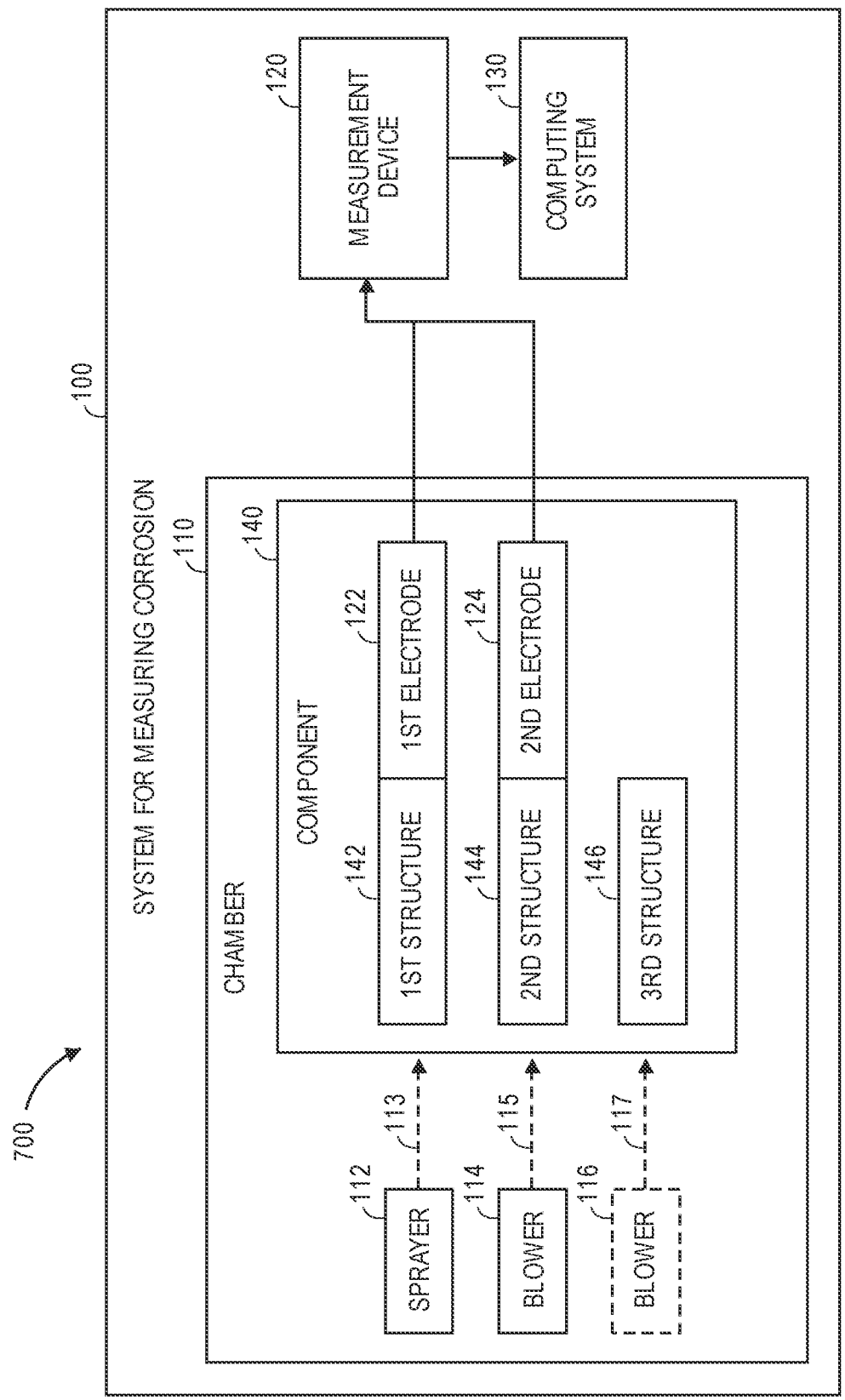
FIG. 7 illustrates a functional block diagram of the system for measuring corrosion on a component.

FIG. 7 illustrates a functional block diagram 700 of the system for measuring corrosion on a component 140. The component 140 can be placed into the chamber 110. Once in the chamber, the sprayer 112 can spray the component 140 with a liquid 113, the blower 114 can blow the component 140 with gas 115, and/or the blower 116 can blow the component 140 with gas 117. This can be part of a cyclic corrosion test that simulates an environment to which the component 140 may be exposed when in use. During or after the cyclic corrosion testing, the measurement device 120 may receive data/measurements (e.g., from the first and second electrodes 122, 124 that are coupled to the component 140—see FIGS. 1-3). The data/measurements may be transmitted to the computing device 130, which may generate results (e.g., see the graphs in FIGS. 5 and 6) based at least partially upon the data measured by the measurement device 120. The results may indicate, for example, a degree of galvanic corrosion on the component 140.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

While the present teachings have been illustrated with respect to one or more implementations, alterations and/or modifications can be made to the illustrated examples without departing from the spirit and scope of the appended claims. In addition, while a particular feature of the present teachings may have been disclosed with respect to only one of several implementations, such feature may be combined with one or more other features of the other implementations as may be desired and advantageous for any given or particular function. As used herein, the term "at least one of A and B" with respect to a listing of items such as, for example, A and B, means A alone, B alone, or A and B. Those skilled in the art will recognize that these and other variations are possible. Furthermore, to the extent that the terms "including," "includes," "having," "has," "with," or variants thereof are used in either the detailed description and the claims, such terms are intended to be inclusive in a manner similar to the term "comprising." Further, in the discussion and claims herein, the term "about" indicates that the value listed may be somewhat altered, as long as the alteration does not result in nonconformance of the process or structure to the intended purpose described herein. Finally, "exemplary" indicates the description is used as an example, rather than implying that it is an ideal.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompasses by the following claims.

What is claimed is:

1. A system for measuring corrosion, comprising:
a first electrode configured to be connected to a first structure; and
a second electrode configured to be connected to a second structure, wherein the first and second structures are galvanically-coupled together, wherein the first and second structures are made of different materials, and wherein the second structure comprises plastic;
a cyclic corrosion chamber configured to run through one or more testing cycles while the first electrode, the first structure, the second electrode, and the second structure are positioned inside the chamber, wherein the one or more testing cycles comprise a wet cycle and a dry cycle, wherein the first and second structures are configured to be sprayed with a liquid solution during the wet cycle, and wherein the first and second structures are configured to be blown with air during the dry cycle; and
a measurement device configured to receive data from the first and second electrodes and to measure one or more parameters based at least partially upon the data, wherein a level of corrosion on the first structure, the second structure, or both is configured to be determined based at least partially upon the one or more parameters.

2. The system of claim 1, wherein the measurement device is positioned outside of the chamber.

3. The system of claim 1, wherein the first structure comprises a honeycomb structure made of metal.

4. The system of claim 1, wherein the second structure comprises a plate made of the plastic.

5. The system of claim 1, wherein the first structure comprises a honeycomb structure made of aluminum, and wherein the second structure comprises a plate made of carbon-fiber reinforced plastic.

6. The system of claim 1, wherein the second structure has a plurality of perforations formed therethrough.

7. The system of claim 1, wherein:
the measurement device comprises a potentiostat,
the first electrode comprises a working electrode,
the second electrode comprises a reference electrode, and
the one or more parameters comprise a voltage difference between the first and second structures.

8. The system of claim 1, wherein the one or more testing cycles further comprise a humid cycle, and wherein air blown during the humid cycle has a greater humidity than the air blown during the dry cycle.

9. The system of claim 1, wherein the first and second structures are part of a component in a vehicle.

10. The system of claim 1, wherein the first and second structures are part of a component in an aircraft.

11. A system for measuring corrosion, comprising:
a first electrode configured to be connected to a first structure, wherein the first structure is a honeycomb structure comprising aluminum;
a second electrode configured to be connected to a second structure, wherein the second structure is a plate made of carbon-fiber reinforced plastic, and wherein the first and second structures are galvanically-coupled together;
a cyclic corrosion chamber configured to run through a wet cycle and a dry cycle while the first electrode, the first structure, the second electrode, and the second structure are positioned inside the chamber, wherein the first and second structures are configured to be sprayed with a liquid solution during the wet cycle, wherein the first and second structures are configured to be blown with air during the dry cycle; and
a potentiostat configured to receive data from the first and second electrodes and to measure a voltage difference between the first and second structures based at least partially upon the data, wherein a level of corrosion on the first structure, the second structure, or both is configured to be determined based at least partially upon the voltage difference.

12. The system of claim 11, wherein the solution comprises a liquid salt solution having a temperature from about 30° C. to about 40° C. during the wet cycle, and wherein the first and second structures are configured to be blown with the air having a temperature from about 20° C. to about 50° C. during the dry cycle.

13. The system of claim 12, wherein the liquid salt solution comprises 5% NaCl pH 3 acetic acid (HAc).

14. The system of claim 12, wherein the chamber is also configured to run through a humid cycle while the first electrode, the first structure, the second electrode, and the second structure are positioned inside the chamber, and wherein air blown during the humid cycle has a greater humidity than the air blown during the dry cycle.

15. A method for measuring corrosion, comprising:
connecting a first electrode to a first structure;
connecting a second electrode to a second structure, wherein the first and second structures are galvanically-coupled together, wherein the first and second structures are made of different materials, and wherein the first electrode or the second electrode comprises a reference electrode;
positioning the first electrode, the first structure, the second electrode, and the second structure in a cyclic corrosion chamber;
running one or more cycles in the chamber, wherein the one or more cycles comprise a wet cycle and a dry cycle, wherein the first and second structures are configured to be sprayed with a liquid solution during the wet cycle, wherein the first and second structures are configured to be blown with air during the dry cycle;
measuring one or more parameters related to the first and second structures based on data received from the first and second electrodes, wherein a level of corrosion on the first structure, the second structure, or both is configured to be determined based at least partially upon the one or more parameters.

16. The method of claim 15, wherein the first structure and the second structure are part of a component that also includes a third structure, wherein the first structure is coupled to and positioned between the second and third structures, and further comprising cutting through the first structure to create first and second portions of the component, the first portion of the component including a first portion of the first structure coupled to the second structure, and the second portion of the component including a second portion of the first structure coupled to the third structure.

17. The method of claim 16, wherein positioning the first and second structures in the chamber comprises positioning the first portion of the component in the chamber.

18. The method of claim 17, further comprising applying a sealant to a connection between the first electrode and the first structure before the first portion of the component is positioned in the chamber.

19. The method of claim 15, wherein the level of corrosion is configured to be measured in real-time when the first structure and the second structure are in part of an aircraft that is in flight.

\* \* \* \* \*